United States Patent [19]

Borninkhof et al.

[11] Patent Number: 5,571,943
[45] Date of Patent: Nov. 5, 1996

[54] PROCESS FOR PREPARING PRIMARY AMINES AND CATALYST SYSTEM SUITABLE THEREFOR

[75] Inventors: Frederik Borninkhof, Nieuwegein; John W. Geus, Bilthoven; Michiel J. F. M. Verhaak, Alkmaar, all of Netherlands

[73] Assignee: Engelhard De Meern B.V., De Meern, Netherlands

[21] Appl. No.: 411,388

[22] Filed: Mar. 28, 1995

Related U.S. Application Data

[63] Continuation of Ser. No. 45,817, Apr. 9, 1993, abandoned.

[30] Foreign Application Priority Data

Apr. 13, 1992 [NL] Netherlands ............................ 9200685
Jul. 17, 1992 [NL] Netherlands ............................ 9201291

[51] Int. Cl.$^6$ .................................................. C07C 209/48
[52] U.S. Cl. ............................ 564/493; 564/490; 564/491; 564/492
[58] Field of Search .................................. 564/490, 491, 564/492, 493

[56] References Cited

U.S. PATENT DOCUMENTS

| | | | |
|---|---|---|---|
| 3,891,707 | 6/1975 | Waddan | 564/498 |
| 3,987,099 | 10/1976 | Hockele et al. | 260/584 |
| 5,132,427 | 7/1992 | Koehler et al. | 564/491 |

FOREIGN PATENT DOCUMENTS

| | | |
|---|---|---|
| 0316761 | 5/1989 | European Pat. Off. . |
| 0322760 | 7/1989 | European Pat. Off. . |
| 0340848 | 11/1989 | European Pat. Off. . |
| 0424738 | 5/1991 | European Pat. Off. . |
| 0482732 | 4/1992 | European Pat. Off. . |
| 0490382 | 6/1992 | European Pat. Off. . |
| 2194685 | 5/1988 | France . |
| 902616 | 1/1954 | Germany . |
| 1193671 | 5/1965 | Germany . |
| 1518118 | 11/1969 | Germany . |
| 1123032 | 8/1968 | United Kingdom . |

OTHER PUBLICATIONS

Greenfield, I & EC Product Research and Development, "Catalytic Hydrogenation of Butyronitrile," vol. 6, No. 2, pp. 142–144 (1967).

*Primary Examiner*—Brian M. Burn
*Attorney, Agent, or Firm*—Weingarten, Schurgin, Gagnebin & Hayes

[57] ABSTRACT

This invention relates to a process for preparing primary amines by hydrogenation of mono and/or dinitrile with hydrogen in the presence of a nickel and/or cobalt catalyst on support and optionally in the presence of ammonia, this process being characterized in that a nickel and/or cobalt catalyst on support is used, optionally in combination with at least one solid, reaction medium-insoluble cocatalyst, the catalyst and/or the cocatalyst being substantially nonacid.

24 Claims, No Drawings

PROCESS FOR PREPARING PRIMARY AMINES AND CATALYST SYSTEM SUITABLE THEREFOR

This application is a continuation of application Ser. No. 08/045,817, filed Apr. 9, 1993 (now abandoned).

This invention relates to a process for preparing primary amines by hydrogenation of nitriles in the presence of a hydrogenation catalyst.

In the hydrogenation of nitriles, primary, secondary or tertiary amines are obtained, depending on the reaction conditions and the catalyst used, it being noted that generally a mixture of all three types of amines is obtained. Much research has been done on the control of the hydrogenation to one type of amine. The isolation of secondary and tertiary amines requires additional apparatus and costs additional energy. It has been found that an important measure for obtaining sufficient selectivity to primary amines is the addition of ammonia to the reaction mixture. By adding ammonia, the deammoniation of primary amines is pushed back, so that the selectivity to primary amines increases. The hydrogenation of dinitriles may present the problem that condensation reactions occur which give rise to cyclic products.

The nature of the catalyst also affects the selectivity of the hydrogenation of nitriles. In fact, it has been found that Raney nickel is a very selective catalyst.

Raney nickel, however, has a number of less desirable properties. Raney nickel is comparatively difficult to handle, which renders its use less attractive. Moreover, environmental objections are associated with its preparation and application. The fact is that its production yields undesired waste water, while prior to its use Raney nickel must generally be treated with an organic solvent. Both aspects are less desirable from an environmental point of view. Finally, it can be noted that Raney nickel exhibits a relatively low activity compared with supported catalyst.

The methods according to the prior art, starting from a catalyst on support, exhibit the disadvantages of a lower selectivity and often poor sedimentation properties.

An overview of a number of known methods for the hydrogenation of nitriles to amines is given by Volf et al in Chapter 4 of Studies in Surface Science and Catalysis, 27, Catalytic Hydrogenation, Hydrogenation of Nitriles, pp. 105–144. From this articles, it appears inter alia that the view is that the nature of the metal is essential to obtaining the desired selectivity, while the effect of the support is not significant.

To increase the selectivity to primary amines, i.e., to suppress condensation reactions, it has been proposed inter alia to add a lye solution to the reaction mixture in liquid-phase hydrogenation, as described in U.S. Pat. No. 2,287, 219. This, however, has been found to give rise to the formation of by-products which are hard to remove from the reaction mixture. Moreover, for the application of supported catalysts, this is by no means always possible because a number of current support materials, such as aluminum oxide and silicon dioxide, are not resistant to lye.

It has also been proposed to add $NH_3$, water or a combination thereof to the reaction mixture (GB-A 1,321, 981). It appears from the cited article by Volf et al that the use of water has an effect only with unsupported cobalt catalysts.

European patent application 340 848 relates to a process for the hydrogenation of nitriles using a nickel catalyst on a support which contains silicon oxide and magnesium oxide. In the Examples of this patent application, a good selectivity to primary amines is described. This selectivity, however, is a result of the reaction conditions employed and not of the nature of the catalyst, as appears from the comparative examples given hereinbelow.

In J. Pasek et al, Collect. Czech. Chem. Commun., Vol.46, (1981), page 1011, mention is made of the use of soda in a small amount in combination with a cobalt catalyst. It has been found that the use of solid soda does not yield any improvement of the selectivity.

U.S. Pat. No. 3,293,298 discloses the use of an alumina containing polar adsorbent to increase the selectivity to primary amines in nitrile hydrogenation. However, its effect on the selectivity appears to be only marginal.

European patent application No. 316,761 describes the hydrogenation of N, N-dimethylaminopropionitrile with a combination of a hydrogenation-catalyst and an alkaline-earth metal oxide. According to the publication referred to, such a system is used to prevent demethylation of the dimethylamino group.

It should further be noted that the selectivity to primary amines is generally lower in the conversion of unsaturated nitriles into saturated amines than in the conversion into unsaturated amines.

All these aspects of the prior art have had as a consequence that to date, in practice, mainly Raney nickel has been used for the preparation of primary amines.

Accordingly, the object of the present invention is to provide a process for preparing primary amines with a high selectivity, using nickel and/or cobalt catalysts on support, which process does not have the disadvantages that occur when using the catalysts that can be used for the reaction in question according to the prior art.

The present invention is based on the surprising insight that an eminent selectivity to primary amines is obtained by the use of a supported nickel and/or cobalt catalyst, optionally in combination with a solid, i.e., reaction medium-insoluble, cocatalyst, the catalyst and/or cocatalyst being substantially nonacid.

The present invention accordingly relates to a process for preparing primary amines by hydrogenation of mono and/or dinitrile with hydrogen in the presence of a nickel and/or cobalt catalyst on support and optionally in the presence of ammonia, which process is characterized in that a nickel and/or cobalt catalyst on support is used, optionally in combination with at least one solid, reaction medium-insoluble, cocatalyst, the catalyst and/or the cocatalyst being substantially nonacid.

It has been found that with such a process a good activity for the hydrogenation is obtained in combination with a high selectivity to the primary amine. The amount of nitrile which is converted into primary amine is generally at least 50%, more particularly at least 85% of the amount of nitrile used.

According to the invention, therefore, a catalyst system is used which consists either of a catalyst that is nonacid, or of a combination of a catalyst and a cocatalyst, the catalyst and/or the cocatalyst being nonacid. More particularly, the mixture of catalyst and cocatalyst has a selectivity of at least 1.5.

The selectivity as defined within the framework of the use of a combination of a catalyst and a cocatalyst according to the present invention, is the difference between the amount of primary amine in weight percent obtained with the combination of catalyst and cocatalyst, less the amount of primary amine in weight percent obtained without cocatalyst at the time when the iodine value is 5.0 under the conditions as defined in the Conditions C described in the Examples.

According to one embodiment, the process according to the invention is characterized by the use of a catalyst system which contains a specific, nonacid, cocatalyst. The effect of the catalyst system is that the formation of by-products decreases by at least 15% (on a weight basis) in the hydrogenation of nitrile to primary amine under the conditions described in the Examples. In general, this will even be more, for instance 20% or even 40%.

It has been found that, as a solid cocatalyst, with success use can be made of solid metal compounds, such as solid metal salts and solid metal oxides. It is particularly surprising that through such a comparatively simple adaptation of the process, a considerable improvement of the selectivity can be obtained while maintaining the activity.

Within the broadest definition, it is possible to use as cocatalyst a solid substance, i.e., a compound that is not soluble in the reaction medium, that is not acid. In general, a catalyst system that contains a non-acidically reacting cocatalyst will exhibit a selectivity of at least 1.5.

As already indicated, as cocatalyst, preferably a metal salt or metal oxide is used. The term 'solid' is used in this connection to indicate that the cocatalyst substantially does not dissolve in the reaction system, i.e., not more than 10%, more particularly not more than 1%, of the solid substance goes into solution in the reaction medium.

In practice, as metals in the salts or oxides, practically all metals from the Periodic System of the Elements can be used, although, naturally, the requirements of the present invention with regard solubility and selectivity must be satisfied. Preferably, however, salts or oxides of alkali and alkaline-earth metals are used.

Suitable substances include the alkaline-earth metal oxides, such as calcium oxide and magnesium oxide, as well as various metal salts. Surprisingly, it has been found that cocatalysts obtained by decomposition of alkali and alkaline-earth metal carboxylates, such as oxalates, are particularly suitable. In the case of alkali metals, such cocatalysts mainly consist of alkali metal carbonates. In the case of alkaline-earth metals, they are mainly oxides.

It has been found that the activity of such alkali metal carbonates as cocatalyst is not only based on the presence of alkali metal carbonate, since the use of pure alkali metal carbonate hardly leads to a positive result, if at all.

Within the framework of the present invention, it is accordingly preferred to use as cocatalyst a solid substance selected from the group consisting of magnesium oxide, calcium oxide and the decomposition products of potassium oxalate, the metal oxides also having been preferably obtained from the carboxylates, more particularly the oxalates thereof.

The amount of cocatalyst affects the selectivity and the activity. Suitable amounts are between 0.05 and 1.5 g cocatalyst per gram of nickel and/or cobalt used. More particularly, these amounts are between 0.1 and 1.0 gram, most preferably between 0.1 and 0.5 gram per gram of nickel and/or cobalt.

The mixture of catalyst and cocatalyst is obtained by mixing particles of the catalyst and the cocatalyst. The particle size of the catalyst and the cocatalyst depends mainly on the nature of the reactor. Suitable particle sizes vary between powdered form, i.e., from 0.1 μm, to pellets of ¼ inch.

It is also possible, however, to process catalyst and cocatalyst into combined particles, using conventional processes for the manufacture of shaped catalyst bodies.

Optionally, the mixture of the catalyst and the cocatalyst can be included in a fat, a nitrile, an amine, or another suitable matrix.

The catalyst used according to the invention is a catalyst on support, which, from the point of view of process economy and process conditions, has great advantages over the use of Raney nickel or cobalt. In the first place, because of the presence of a support, less nickel is required, while moreover a supported catalyst is much easier to handle. Such a catalyst can be used particularly readily for the hydrogenation in a (fixed) catalyst bed, which is more difficult with Raney nickel or cobalt.

The catalyst accordingly consists of an active component, nickel and/or cobalt, optionally in combination with another hydrogenating metal component and a support. The catalyst in reduced form contains substantially no acid sites.

In the embodiment with a cocatalyst, the catalyst may be nonacid; however, this is not required. If no cocatalyst is used, nonacidity of the catalyst is essential.

There are a number of processes for obtaining such a nonacid catalyst. In the first place it is possible to start from a support which is acid or has become acid by the provision of one or more (precursors of) active components. Prior to use, such a catalyst must be treated with a promoter compound which imparts nonacid properties to the catalyst, in order to obtain a suitable catalyst. In the case where the support is not acid nor becomes acid through reaction with the (precursor of the) active component, no further steps are required.

It has been found that the catalysts which have been rendered less acid by treatment with at least one compound give the best results with respect to selectivity to primary amines. Accordingly, such catalysts are preferred.

Compounds derived from alkali metals and alkaline-earth metals give a surprisingly high selectivity and they are preferred. Suitable compounds are salts and hydroxides of sodium, potassium, magnesium, calcium, barium and lanthanum. Suitable salts are carbonates, halogenides, such as chlorides, and nitrates. Mixtures of such compounds can be used as well. Generally, the amount used must be so large that the catalyst is not acid. In practice, the amount will accordingly depend on the nature of the catalyst and the nature of the compound. With the above-mentioned metals, this amount, calculated as metal relative to the catalyst, will be between 0.1 and 15 wt. %, more particularly between 0.5 and 7.5 wt %.

The catalysts can be prepared in a known manner, apart from any steps necessary for obtaining the nonacid character of the catalyst.

Various methods for the preparation of nickel and/or cobalt catalysts are known. Examples of methods of preparation are the methods based on impregnation of preformed supports with a nickel and/or a cobalt compound, the precipitation of support and the active component from one or more solutions thereof and the deposition-precipitation of the active component on a support which may or may not be preformed. The impregnation methods are described in detail by Lee and Aris in "Preparation of Catalysts III", Eds Poncelet et al, Elsevier 1983, page 35. Another method for the preparation of the catalysts is the precipitation of the support and the active component from one or more solutions thereof. Such a precipitation can occur simultaneously or in succession (D. C. Puxley et al, "Preparation of Catalysts III", Eds. Poncelet et al, Elsevier 1983, page 237). The deposition-precipitation of the active component on a support which may or may not be preformed has been described in detail, for instance by Schaper et al in "Preparation of Catalysts III", eds. Poncelet et al, Elsevier 1983, page 301.

After the nickel and/or cobalt compound has been provided on the support, the catalyst is optionally calcined and, prior to use, reduced.

If the starting material is a catalyst which acquires the nonacid property by treatment with a promoter compound, this treatment can be carried out in any desired stage of the preparation.

After reduction, i.e., in the active form, the catalyst preferably comprises 1–95 weight parts of support and 5–99 weight parts of metallic nickel. In most cases, non-reduced nickel is also present. According to the invention, known supports can be used, such as silica, alumina, magnesium oxide, calcium oxide and combinations thereof, optionally in combination with promoting components.

For determining the acid or nonacid character of the catalyst, a number of methods are available. The most accurate method is to assay the degree of conversion of propylamine into dipropylamine in the gas phase at 125° C. The implementation of this assay is presented in the Examples. The conversion should not be more than 15% of the propylamine, preferably not more than 10% and in particular not more than 5%. It was found that such an assay is a very accurate and unequivocal measure for the acidity or nonacidity of the catalyst.

A slightly less accurate but also eminently practicable method is the temperature programmed desorption of $NH_3$ from the catalyst. This method is well known and can be implemented in a simple manner by a person of ordinary skill in the art (see also: Falconer & Schwarz, Catalysis Review, Vol. 25(2), 1983, page 141).

The hydrogenation of nitriles can be carried out in various ways, under conventional conditions with respect to temperature, pressure, nickel content and the like. Suitable conditions are a hydrogen pressure of from 1 to 100 bar, a $NH_3$ pressure (if $NH_3$ is used) of from 0.5 to 40 bar, with a total pressure not exceeding 100 bar. The temperature in the hydrogenation is preferably between 75° and 225° C. In the case where the hydrogenation is carried out in slurry phase, the amount of catalyst is preferably from 0.01 to 5 wt. %, calculated as nickel relative to the amount of nitrile. The nitriles to be hydrogenated can be all suitable organic nitriles, such as nitriles with a short chain, for instance acetonitrile or propionitrile, and nitriles with longer chains, such as those derived from fatty acids. Especially the nitriles derived from fatty acids and typically obtained by treatment of fatty acid with $NH_3$, are commercially of great importance as intermediates for all kinds of chemical end products. Such nitriles generally have 8–22C atoms. Another group of nitriles which can be hydrogenated to advantage according to the invention consists of nitriles having more than one nitrile group in the compound, such as adiponitrile and succinonitrile. The great advantage with these compounds resides in the suppression of condensation reactions, which may give rise to ring formation.

More generally, the nitriles to be used can be defined as compounds of the formula R—CN or R'—$(CN)_2$, wherein R and R' represent hydrocarbon radicals with a $C_2$ to $C_{10}$ chain, which may or may not be saturated. It is noted here that compounds of the type as described in European patent application No. 316,761, when a combination of a catalyst and a cocatalyst is used, are not included according to the invention. More particularly, the hydrogenation of N, N-dimethylaminopropionitrile with a combination of a hydrogenation catalyst and an alkaline-earth metal oxide is not included. The fact is that according to the above-mentioned publication, such a system is used for the prevention of demethylation of the dimethylamino group, which is an effect that does not play any role at all according to the present invention since the present invention is directed to the improvement of the selectivity in the hydrogenation.

An important advantage of the present invention, and particularly of the variant where a nonacid catalyst is worked with, resides in the possibility which has been created of carrying out the selective hydrogenation of nitrile to primary amine in the absence of ammonia. It is true that the selectivity decreases somewhat as a result, but it still remains at a very acceptable level. The advantage of the fact that it is not necessary to use ammonia is of course evident. It is noted that with the conventional catalysts, an acceptable selectivity is obtained only in the presence of ammonia. Without $NH_3$ the formation of by-products, such as secondary and tertiary amines is prohibitively high.

The invention will now be elucidated in and by a number of examples without being limited thereto.

EXAMPLES

1. Description Autoclave and Reaction Conditions

The hydrogenations were carried out in a 1 liter autoclave with an internal diameter of 76 mm and a height of 229 mm. The reactor is provided with a dispersionmax mixing device, consisting of a turbine mixing paddle mounted on a hollow shaft. The reactor is provided with baffles. Via the hollow shaft of the agitating device, the hydrogen is introduced into the autoclave and dispersed in the liquid.

The temperature of the reactor is set by means of a temperature control which controls an electric heating jacket. The temperature in the autoclave is measured with a thermo couple and the pressure is measured with a manometer.

Introduced into the autoclave are 500 g unsaturated tallow nitrile with the catalyst suspended therein. The tallow nitrile used has an iodine valve between 50 and 60, a free fatty acid content of maximally 0.15 wt. %, an amide content of maximally 0.5 wt. % and contains maximally 0.1 wt. % water. The amount of catalyst has been chosen such that the nickel and/or cobalt content in the autoclave varies from 0.25 g to a maximum of 5 g.

The hydrogenation process is carried in a two-step reaction; first the nitrile group is hydrogenated and subsequently, if so desired at a higher temperature, the carbon chain is saturated.

After the reaction mixture has been introduced into the autoclave, the autoclave is rinsed three times with nitrogen by increasing the pressure in the autoclave to 5 bar and subsequently letting off the pressure to 1 bar. This procedure is subsequently repeated twice with the agitator switched on (1400 revolutions per minute). After the autoclave has been evacuated, 35 g liquid ammonia is introduced into the autoclave at 30° C. Then the reactor is heated to the desired reaction temperature. As soon as the desired reaction temperature has been achieved, the desired ammonia partial pressure is set by letting off the excess ammonia. Then the desired total pressure is set by supplying hydrogen, which at the same time sets off the reaction. The pressure of the reaction mixture is maintained through a continuous hydrogen supply from a high-pressure storage cylinder, the temperature and pressure of which are registered as a function of the reaction time. With these data, the hydrogen consumption during the reaction, and hence the conversion, can be measured.

As soon as the theoretically required amount of hydrogen for the hydrogenation of the nitrile group has been incorporated and the hydrogen consumption has fallen below 0.2 normal liter per minute, the reaction is considered as completed. At this time, a sample of the autoclave content is taken via a sampling valve present for that purpose. The temperature is now raised for carrying out the second reaction step, being the hydrogenation of the unsaturated carbon—carbon bond. For implementing this second reaction step, the partial ammonia pressure is removed by letting off the pressure of the reactor volume and subsequently setting the desired hydrogen pressure.

During the hydrogenation of the carbon chain, the hydrogen consumption is also registered. By the end of the reaction, some samples are taken from the autoclave for analyzing the composition of the reaction mixture. The total reaction time is determined by the total time of both reaction steps, required to reduce the iodine value to 5.0.

The tests were carried out under different reaction conditions.

Conditions A: Preparation Unsaturated Primary Amines (Single-Step Reaction with Ammonia and Hydrogen)

Temperature: 140° C.

Pressure: 10 bar $NH_3$+20 bar $H_2$

Nickel concentration: 0.2%

Conditions B: Preparation Unsaturated Primary Amines (Single-Step Reaction with Hydrogen Alone)

Temperature: 140° C.

Pressure: 30 bar $H_2$

Nickel concentration: 0.2%

Conditions C: Preparation Saturated Primary Amines (Two-Step Reaction with Ammonia and Hydrogen)
Step 1

Temperature: 130° C.

Pressure: 18 bar $NH_3$+36 bar $H_2$

Nickel concentration: 0.2%
Step 2

Temperature: 175° C.

Pressure: 54 bar $H_2$

Nickel concentration: 0.2%

2. Catalyst Preparation

The catalysts tested were prepared through incipient wetness impregnation of a powdered support material. An overview of the various preparation procedures is given below.

Preimpregnation

Impregnation of the support material with one (or more) promoter salt(s); drying in the air at 120° C. for 16 h. Heating in the air at 550° C. for 2 h. Providing nickel and/or cobalt salt via incipient wetness; drying at 120° C. for 16 h and calcining at 375° C. for 1.5 h. Reduction at a suitable temperature in 100% hydrogen for 2 h.

Coimpregnation

Simultaneous impregnation of the support with one (or more) promoter salt(s) and nickel and/or cobalt salt. Drying in the air at 120° C. for 16 h. followed by calcination at 375° C. for 1.5 h. Reduction at a suitable temperature in 100% hydrogen for 2 h.

Postimpregnation

Impregnation of the support with nickel and/or cobalt salt followed by drying in the air at 120° C. for 16 h. Impregnation with one (or more) promoter salt(s); drying in the air at 120° C. for 16 h and calcining at 375° C. for 2 h. Reduction at a suitable temperature in 100% hydrogen for 2 h.

The Table below gives an overview of the various catalysts with respect to the preparation, composition and coding. All catalysts contain 20% nickel.

| Code | Preparation | Support | Promotors |
|---|---|---|---|
| 1A | Imp. | SiAl | — |
| 1B | Pre-imp. | SiAl | 10% Potassium |
| 2A | Imp. | Al | — |
| 2B | Pre-imp. | Al | 3% Potassium |
| 2C | Pre-imp. | Al | 4% Potassium |
| 2D | Pre-imp. | Al | 5% Potassium |
| 2E | Co-imp. | Al | 3% Potassium |
| 2F | Post-imp. | Al | 3% Potassium |
| 3A | Pre-imp. | Al | 4% Magnesium |
| 3B | Pre-imp. | Al | 7% Magnesium |
| 4A | Pre-imp. | Al | 4% Calcium |
| 4B | Pre-imp. | Al | 7% Calcium |
| 4C | Pre-imp. | Al | 10% Calcium |
| 5A | Pre-imp. | Al | 4% Sodium |
| 6A | Pre-imp. | Al | 1% Potassium + 3% Calcium |
| 6B | Pre-imp. | Al | 2% Potassium + 2% Calcium |
| 6C | Pre-imp. | Al | 3% Potassium + 1% Calcium |
| 6D | Co-imp. | Al | 2% Potassium + 2% Calcium |

With the exception of the catalysts 1A and 2A, all catalysts are nonacid.

In addition to these catalysts, a Raney nickel catalyst was tested as well.

3. Test Results

The test results of the various catalysts under the different conditions are specified hereinbelow.

3.1 Test Conditions A

The results obtained with the conditions mentioned under A:

| Catalyst | Raney Ni | 2A | 2C | 2D |
|---|---|---|---|---|
| PA [wt %] | 93.3 | 89.6 | 93.7 | 96.1 |
| SA and TA [wt %] | 6.7 | 10.4 | 6.3 | 3.9 |
| IV | 38 | 43 | 32 | 29 |
| Time [min] | 255 | 85 | 165 | 320 |
| Conversion [%] | 94.2 | 99.9 | 99.8 | 97.1 |

Abbreviations used:
PA = Primary Amines
SA and TA = Secondary Amine and Tertiary Amine
IV = Iodine Value With increasing Potassium content, a very clear selectivity improvement can be observed. The activity decreases slightly.

3.2 Test Conditions B

The results obtained with the conditions mentioned under B

| Catalyst | 1A | 1B | 2A | 2C | 2D |
|---|---|---|---|---|---|
| PA [wt %] | 64.2 | 79.3 | 70.8 | 81.2 | 89.6 |
| SA and TA [wt %] | 35.8 | 20.7 | 29.2 | 18.8 | 10.4 |
| IV | 42 | 18 | 1 | 22 | 12 |
| Time [min] | 115 | 390 | 75 | 160 | 350 |
| Conversion [%] | 98.2 | 87.8 | 99.5 | 98.8 | 96.6 |

Under these test conditions, too, without ammonia partial pressure, a clear selectivity improvement can be observed as soon as the support is promoted with Potassium. The reaction time increases with increasing Potassium content.

3.3 Test Conditions C
Results obtained with the conditions mentioned under C:

| Catalyst | Raney Ni | 2A | 2B | 2C | 2E | 2F |
|---|---|---|---|---|---|---|
| PA [wt %] | 91.4 | 88.3 | 92.5 | 94.6 | 93.5 | 92.0 |
| SA and TA [wt %] | 8.6 | 11.7 | 7.5 | 5.4 | 6.5 | 8.0 |
| IV | 5 | 5 | 5 | 5 | 5 | 5 |
| Time [min] | 295 | 145 | 180 | 225 | 170 | 165 |

Clear improvement of selectivity under the influence of Potassium promotion of the support, with preimpregnation, coimpregnation as well as postimpregnation.

| Catalyst | Raney Ni | 2A | 3A | 3B |
|---|---|---|---|---|
| PA [wt %] | 91.4 | 88.3 | 90.0 | 91.5 |
| SA and TA [wt %] | 8.6 | 11.7 | 10.0 | 8.5 |
| IV | 5 | 5 | 5 | 5 |
| Time [min] | 295 | 145 | 120 | 145 |

Magnesium has a positive effect on the selectivity and, at low contents, an activity-increasing effect as well.

| Catalyst | Raney Ni | 2A | 4A | 4B | 4C |
|---|---|---|---|---|---|
| PA [wt] | 91.4 | 88.3 | 91.3 | 92.2 | 92.2 |
| SA and TA [wt %] | 8.6 | 11.7 | 8.7 | 7.8 | 7.8 |
| IV | 5 | 5 | 5 | 5 | 5 |
| Time [min] | 295 | 145 | 100 | 125 | 210 |

Calcium also has a positive effect on the selectivity (conversion of propylamine 4.8 mol %), while in this case, too, the activity improves clearly at low Calcium concentrations.

| Catalyst | Raney Ni | 2A | 5A |
|---|---|---|---|
| PA [wt %] | 91.4 | 88.3 | 94.5 |
| SA and TA [wt %] | 8.6 | 11.7 | 5.5 |
| IV | 5 | 5 | 5 |
| Time [min] | 295 | 145 | 135 |

For sodium, an increased selectivity to primary amines was measured.

Finally, a number of combinations of Potassium and Calcium were investigated.

| Catalyst | 2A | 6A | 6B | 6C | 6D |
|---|---|---|---|---|---|
| PA [wt %] | 88.3 | 92.5 | 93.5 | 94.4 | 93.5 |
| SA and TA [wt %] | 11.7 | 7.5 | 6.5 | 5.6 | 6.5 |
| IV | 5 | 5 | 5 | 5 | 5 |
| Time [min] | 145 | 110 | 150 | 190 | 175 |

The combination of Potassium and Calcium has a positive effect on the selectivity to primary amines and with a proper combination of the two promoters a good activity can be obtained at the same time.

4. Gas Phase Hydrogenation of Propionitrile to Propylamine

The gas phase hydrogenations of propionitrile to propylamine were carried out in a microreactor having an internal diameter of 1 cm.

The propionitrile feed was saturated at 30° C. and subsequently cooled to 20° C. The vapor pressure of propionitrile at 20° C. is 48 mbar and at a total pressure of 850 mb in the reactor system, this results in a volume concentration of 5.6% propionitrile in the gas stream. The reactor and the sample loop were collectively maintained at a constant temperature of 50° C. so as to prevent condensation of products in the lines. The gases used were dried before the microreactor and rendered oxygen-free over filters. The gas flows were controlled with mass flow controllers (Brooks).

For the tests, a sieve fraction of the catalysts was taken, with a diameter of 0.425–0.85 mm. The amount of nickel in the reactor was kept constant at 12.5 mg. The catalyst was reduced in situ in the reactor with 100% hydrogen (75 ml/min). After the reduction, the catalyst was cooled and propionitrile was passed over the catalyst bed, whereafter the temperature was gradually increased. Samples of the gas mixture were taken regularly and analyzed on a gas chromatograph (column; Tenax TA 60–80 mesh).

Catalyst Preparation

The following catalysts were prepared:

| | |
|---|---|
| Alk-00 | 5 wt % Nickel on Alumina |
| Alk-02 | 5 wt % Nickel and 2 wt % Potassium on Alumina |
| Alk-05 | 5 wt % Nickel and 5 wt % Potassium on Alumina |
| Alk-08 | 5 wt % Nickel and 8 wt % Potassium on Alumina |

First Potassium was provided on the powdered support via incipient wetness impregnation, whereafter the support was dried in the air at 120° C. for 16 h. Subsequently, a calcination was carried out in the air at 550° C. for 5 h. Nickel was also provided on the powdered support via incipient wetness and subsequently dried at 120° C. for 16 h. The catalyst thus obtained was pressed into granules and subsequently ground to the desired sieve fraction. This sieve fraction was introduced into the quartz reactor and the catalyst was activated in situ.

Test Results

With the four above-mentioned catalysts, the following results were measured at 160° C. and upon complete conversion.

| Catalyst | PA* | DPA* | TPA* |
|---|---|---|---|
| Alk-00 | 66 | 33 | 1 |
| Alk-02 | 72 | 28 | — |
| Alk-05 | 93 | 7 | — |
| Alk-08 | 96 | 4 | — |

*Mol %
The following abbreviations are used:
PA = propylamine
DPA = dipropylamine
TPA = tripropylamine It is clear to see that the selectivity to primary amines increases as soon as the catalyst is promoted with Potassium.

COMPARATIVE EXAMPLE

A number of catalysts were tested with the conditions C, only the first reaction step. Catalyst 7A corresponds to the catalysts described in European patent application 340,848. The molar $SiO_2/Ni$ ratio was 0.19 and the molar $MgO/Ni$ ratio was 0.1. The pore volume was 0.45 ml/g, determined with $N_2$ adsorption, while the pore diameter was 5.6 nm, calculated with the formula $$\text{average pore diameter} = (4000 * PV)SA$$

The BET surface was 320 m²/g and the specific nickel surface was 95 m²/g nickel.

The extent of conversion of propylamine to condensation products thereof, using the catalyst 7A, was 16.5 mol % at 125° C. For the catalyst 2D used for comparison, this was 0%.

The other catalysts serve for elucidation of the use of cobalt as active component.

| Code | Preparation | Support | Ni/Co | Promoters |
|------|-------------|---------|-------|-----------|
| 7A | Precipitation | Si | Ni | Mg |
| 8A | Imp. | Al | Co | — |
| 8B | Pre-imp | Al | Co | 3% Potassium |

As appears from the following table, the magnesium-containing catalyst is clearly less selective under the conditions employed for this test than Raney nickel.

| Catalyst | Raney Ni | 7A | 2D |
|----------|----------|------|------|
| PA [wt %] | 95.1 | 93.4 | 96.0 |
| SA and TA [wt %] | 4.9 | 6.6 | 4.0 |
| IV | 39 | 37 | 28 |
| Time [min] | 245 | 80 | 205 |

The cobalt catalysts were tested under the conditions C

| Catalyst | 8A | 8B |
|----------|------|------|
| PA [wt %] | 84,5 | 88,4 |
| SA and TA [wt %] | 15.5 | 11.6 |
| IV | 5 | 5 |
| Time [min] | 295 | 320 |

Catalyst 9 was prepared by injecting a solution containing both nickel nitrate and magnesium nitrate into a solution of ammonium oxalate (1.5 l) at 50° C. The molar oxolate/(Ni+Mg) ratio was 1 and the amount of nickel was such that a 25 wt. % metal load was obtained in the reduced catalyst. The injection was carried out with vigorous stirring over a period of 90 min. The suspension was subsequently aged for 15 min. The catalyst was obtained by filtering off, washing and drying in the air at 120° C.

Catalysts 10A and 10B were prepared by homogeneous deposition-precipitation of a nickel compound on silica (Aerosil 200 from Degussa AG, 200 m²/g). Urea was added to an aqueous suspension in which nickel salt had been dissolved. After raising the temperature to approx. 70°, decomposition of the urea occurred, which led to precipitation of the nickel compound on the silica. After the precipitation had been completed, the precursor was filtered off, thoroughly washed with hot doubly distilled water and dried overnight at 120° C.

Catalyst 10C was prepared by wet impregnation of the same type of silica with a solution of nickel nitrate in doubly distilled water. The solution was acidified to pH 3 using diluted nitric acid. To 10 gram support, 75 ml solution was added. After stirring for 2 h at room temperature, a light green gel was obtained which was dried overnight at 120° C.

The catalysts 11 and 12, based on an alumina support, were prepared by wet impregnation of a γ-alumina support (aluminum oxide-C; Degussa AG; 100 m²/g). The catalysts were prepared through the use of a two-step impregnation method. In the first step, 10 g alumina support was impregnated with 25 ml water, in which a promoter compound may or may not have been dissolved, stirred at room temperature for two hours and dried overnight at 120° C. The dried support was powdered and subsequently calcined in the air at 550° C. for 5 h. After calcination, the support was impregnated with the solution, which contained the desired amount of nickel nitrate for obtaining a 5 wt. % nickel load on the catalyst after reduction. For impregnation, the pH of the nickel solution was adjusted to 6 using diluted ammonia. After the paste was stirred at room temperature for 2 h, it was dried overnight in the air at 120° C.

The promoting compound which was used for obtaining the desired nonacid character of the catalyst was either added in the first impregnation step or impregnated in the second step together with nickel nitrate.

Catalyst 13 was prepared by injecting at room temperature a concentrated solution (pH-1) with an equimolar amount of aluminum nitrate and ammonium hydrogen phosphate into a reactor which contained 2 l water acidified to pH 3 with nitric acid. With vigorous stirring, the injection of 600 ml solution was carried out within 90 min. After the precipitation was completed, the white precipitate was filtered off and the fresh support was dried overnight at 120° C. After drying, the material was powdered and calcined at 550° C. for 24 h. Utilizing impregnation of the support with an aqueous nickel nitrate solution, pH 6, 1 ml solution/g support, a 5 wt. % nickel on aluminum phosphate catalyst was obtained.

Catalyst 14A was obtained by impregnating a strongly acid aluminum silicate (Engelhard De Meern B. V., A797-06-002-01, 225 m²/g) with such an amount of nickel nitrate solution that 5 wt. % nickel load was obtained. For the preparation of catalyst 14B, the support was first impregnated with a potassium nitrate solution (1 ml/g support), stirred for 2 h and dried overnight in the air at 120° C. The dried support was powdered and calcined at 550° C. for 5 h. The promoted support was impregnated with a nickel nitrate solution (pH 6, 1 ml/g support) stirred for 2 h and dried overnight at 120° C.

TABLE I

| | |
|---|---|
| 25 wt. % Ni/magnesia (ex oxalate) | 9 |
| 5 wt. % Ni/silica (urea decomposition) | 10A |
| 25 wt. % Ni/silica (urea decomposition) | 10B |
| 5 wt. % Ni/silica (impregnation) | 10C |
| 5 wt. % Ni/γ-alumina | 11A |
| 5 wt. % Ni/2 wt. % Na/γ-alumina | 11B |
| 5 wt. % Ni/2 wt. % Ca/γ-alumina | 11C |
| 5 wt. % Ni/2 wt. % Zn/γ-alumina | 11D |
| 5 wt. % Ni/1 wt. % K (ex KNO₃)/γ-alumina | 12A |
| 5 wt. % Ni/2 wt. % K (ex KNO₃)/γ-alumina | 12B |
| 5 wt. % Ni/3 wt. % K (ex KNO₃)/γ-alumina | 12C |
| 5 wt. % Ni/4 wt. % K (ex KNO₃)/γ-alumina | 12D |
| 5 wt. % Ni/2 wt. % K (ex KNO₃)/γ-alumina | 12E |
| 5 wt. % Ni/2 wt. % K (ex KOH)/γ-alumina | 12F |
| 5 wt. % Ni/2 wt. % K (ex K₂CO₃)/γ-alumina | 12G |
| 5 wt. % Ni/aluminum phosphate | 13 |
| 5 wt. % Ni/aluminosilicate | 14A |
| 5 wt. % Ni/10 wt. % K (ex KNO₃)/aluminosilicate | 14B |

The gas phase hydrogenation of acetonitrile was studied in a fully automated microflow reactor which operated at atmospheric pressure.

Prior to the experiments, the catalyst precursors were dried in the reactor in hydrogen (75 ml/min) at 125° C. for 30 min. The reactor temperature was subsequently raised by 2° C./min to 450° C. and maintained at this temperature for 10 h. Thus, reductions of 80–100% and nickel surfaces between 60 and 120 m²/g nickel were obtained.

After reduction, the catalyst was cooled in hydrogen to room temperature. Subsequently, the hydrogen was saturated with acetonitrile at −4° C. and subsequently passed through the fixed catalyst bed. The catalyst bed initially consisted of 0.25 g dried catalyst precursor, i.e., before reduction, while approximately 2.5 vol. % acetonitrile was present in the gas stream.

In the experiments, the reactor temperature was first increased from room temperature to 40°, whereafter the temperature of the catalyst bed was stabilized for 25 min. Then the bed temperature was raised by steps of 5° to 140° C. The formation of primary, secondary and tertiary amines was determined by means of gas chromatography. In the following Table, for each catalyst the selectivity to ethylamine at 125° C. is expressed in mole percent.

TABLE 2

| Catalyst | Selectivity* % | Acidity** % |
|---|---|---|
| 9 | 97.5 | 0 |
| 10A | 56 | 27.3 |
| 10B | 61.0 | 19.5 |
| 10C | 79.4 | 9.8 |
| 11A | 76.1 | 11.0 |
| 11B | 94.0 | 0 |
| 11C | 84.0 | 6.7 |
| 11D | 82 | 3 |
| 12A | 81.0 | 10.1 |
| 12B | 92.7 | 1.6 |
| 12C | 97.2 | 0.9 |
| 12D | 96.8 | 1.0 |
| 12E | 96.5 | 0 |
| 12F | 98 | 0 |
| 12G | 98 | 0 |
| 13 | 27.4 | 42.6 |
| 14A | 38.7 | 36.9 |
| 14B | 93.3 | 1.0 |

*: Mole percent to ethylamine
**: Percent conversion propylamine at 125° C.

Gas Phase Disproportionation of Propylamine

In order to determine the acid or nonacid character of the catalyst, the gas phase disproportionation of propylamine in dipropylamine is studied.

Prior to the catalytic experiments, the precursors were dried in the reactor at 125° C. for 30 min in hydrogen at a rate of 75 ml/min (0.25 g dried catalyst precursor). Then the reactor temperature was raised at a rate of 2° C./min to 450° C. and maintained at this temperature for 10 h while passing through hydrogen (75 ml/min).

After reduction, the reduced catalyst was cooled to room temperature in a hydrogen stream. The hydrogen was subsequently saturated with propylamine at −15° C., so that a concentration of approx. 5.6 vol. % propylamine in gas stream was obtained. The gas mixture was passed through the catalyst bed. The temperature of the catalyst bed was first adjusted from room temperature to 75° C. and stabilized for 25 min. After stabilization the bed temperature was increased by steps of 5 degrees to 175° C. On the basis of the gas chromatographic analysis of the reaction mixture, the extent of disproportionation was determined. The data are included in Table 2; see above. Also indicated is the correlation with the selectivity to ethylamine of the same catalyst.

EXAMPLES 15–25

Employing the conditions C, a number of experiments were carried out with various mixtures of a magnesium-promoted nickel catalyst and a solid cocatalyst.

As cocatalyst, the following components were used.

| Exp. | Cocatalyst | Amount g/g cat |
|---|---|---|
| 15 | Alumina (γ;200 m²/g) | 0.25 |
| 16 | Clay | 0.25 |
| 17 | Active carbon | 0.25 |
| 18 | magnesium hydroxide | 0.25 |
| 19 | potassium carbonate (p.a.) | 0.25 |
| 20 | $Na_2CO_3$ | 0.25 |
| 21 | potassium carbonate (ex oxalate) | 0.25 |
| 22 | id | 1.0 |
| 23 | magnesium oxide (ex oxalate) | 0.25 |
| 24 | magnesium oxide (ex hydroxide) | 0.15 |
| 25 | calcium oxide (ex oxalate) | 0.25 |

The results of these experiments are as follows:

| | First step | | | Second step | | |
|---|---|---|---|---|---|---|
| Exp | T (min) | %* | IV** | T (min) | %* | Selectivity |
| 15# | 80 | 93.3 | 38.0 | 25 | 90.4 | 1.2 |
| 16# | 85 | 93.7 | 39.4 | 30 | 90.6 | 1.4 |
| 17# | 85 | 93.5 | 41.0 | 40 | 90.0 | 0.8 |
| 18# | 80 | 93.3 | 38.0 | 20 | 90.6 | 1.4 |
| 19# | 90 | 93.7 | 39.2 | 30 | 90.4 | 1.2 |
| 20# | 85 | 92.5 | 38.6 | 35 | 89.4 | 0.0 |
| 21 | 90 | 94.2 | 39.8 | 25 | 91.5 | 2.3 |
| 22 | 125 | 97.0 | 36.9 | 20 | 96.4 | 7.2 |
| 23 | 85 | 95.2 | 28.5 | 10 | 93.2 | 4.0 |
| 24 | 85 | 93.9 | 30.9 | 10 | 91.9 | 2.7 |
| 25 | 80 | 93.7 | 27.0 | 10 | 91.5 | 2.3 |

*: weight percent primary amine formed in the corresponding step
**: Iodine Value
: Comparitive Example It clearly appears from these experiments that alumina, clay, active carbon, soda, magnesium hydroxide and p.a. quality potassium carbonate do not meet the requirements of a sufficient selectivity and therefore are not suitable or less suitable as cocatalysts.

We claim:

1. A process for preparing primary amines by hydrogenation of mono and/or dinitrile with hydrogen, comprising the steps of:

providing a mono and/or dinitrile to be hydrogenated;

providing a catalyst comprising nickel and/or cobalt on a support, said catalyst having substantially no acid sites; and hydrogenating said mono and/or dinitrile with hydrogen in the presence of said catalyst, wherein said hydrogenation takes place in a substantially diluent-free environment with respect to said catalyst, said hydrogenation resulting in a high selectivity of primary amine.

2. A process for preparing primary amines by hydrogenation of mono and/or dinitrile with hydrogen, comprising the steps of:

providing a mono and/or dinitrile to be hydrogenated;

providing a catalyst comprising nickel and/or cobalt on a support and a solid, reaction medium-insoluble cocatalyst, said catalyst and cocatalyst being substantially nonacid; and hydrogenating said mono and/or dinitrile with hydrogen in the presence of said catalyst and said cocatalyst, wherein said hydrogenation takes place in a substantially diluent-free environment with respect to said catalyst, said hydrogenation resulting in a high selectivity of primary amine.

3. The process of claim 1, wherein said catalyst having substantially no acid sites is generated by the steps of:

provided an unreduced catalyst; and promoting said unreduced catalyst prior to addition to said hydrogenation reaction with a promotor compound which imparts nonacid properties to said unreduced catalyst, wherein said unreduced catalyst, after promotion, contains substantially no acid sites.

4. The process of claim 1, further comprising the step of reducing said catalyst, wherein said catalyst, prior to said reducing step, does not contain any acid sites, and during said reducing step, no acid sites are generated.

5. The process of claim 1, wherein said mononitrile is a fatty acid nitrile having 8 to 22C atoms.

6. The process of claim 3, wherein said promotor is selected from the group consisting of alkali metal compounds and alkaline-earth compounds.

7. The process of claim 3, wherein said promotor is selected from the group consisting of a magnesium, a sodium, a potassium, and a calcium compound.

8. The process of claim 1, wherein the hydrogenation is carried out in the absence of ammonia.

9. The process of claim 2, wherein the mixture of catalyst and cocatalyst has a selectivity of at least 1.5.

10. The process of claim 2, wherein said cocatalyst is selected from the group consisting of alkali metal compounds and alkaline-earth compounds.

11. The process of claim 10, wherein said cocatalyst comprises an alkaline-earth metal oxide.

12. The process of claim 2, wherein said cocatalyst comprises a decomposition product of an alkali or alkaline-earth metal carboxylate.

13. The process of claim 12, wherein said carboxylate is an oxalate.

14. The process of claim 1, wherein said catalyst, after reduction, has a nickel and/or cobalt content between 1 and 95 weight parts of said catalyst.

15. The process of claim 2, wherein the amount of cocatalyst is between 0.05 and 1.5 gram per gram nickel and/or cobalt.

16. The process of claim 1, wherein said hydrogenation is carried out in a fixed bed reactor or in slurry phase.

17. The process of claim 2, wherein the amount of cocatalyst is between 0.1 and 1.0 gram per gram nickel and/or cobalt.

18. The process of claim 1, wherein said support is chosen from the group consisting of silica, alumina, magnesium oxide, calcium oxide and combinations thereof.

19. The process of claim 12, wherein said carboxylate is potassium oxalate.

20. The process of claim 2, wherein said mononitrile is a fatty acid nitrile having 8 to 22C atoms.

21. The process of claim 2, wherein said hydrogenation is carried out in a fixed bed reactor or in slurry phase.

22. The process of claim 2, wherein said support is chosen from the group consisting of silica, alumina, magnesium oxide, calcium oxide and combinations thereof.

23. The method of claim 1, wherein said hydrogenating step takes place without alkali correction to said catalyst.

24. The process of claim 2, wherein the hydrogenation is carried out in the absence of ammonia.

* * * * *